(12) United States Patent
Corson et al.

(10) Patent No.: US 10,752,901 B2
(45) Date of Patent: Aug. 25, 2020

(54) INHIBITION OF FERROCHELATASE AS AN ANTIANGIOGENIC THERAPY

(71) Applicant: Indiana University Research and Technology Corporation, Indianapolis, IN (US)

(72) Inventors: Timothy Corson, Fishers, IN (US); Halesha Basavarajappa, Indianapolis, IN (US)

(73) Assignee: INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 15/009,339

(22) Filed: Jan. 28, 2016

(65) Prior Publication Data

US 2016/0222388 A1    Aug. 4, 2016

Related U.S. Application Data

(60) Provisional application No. 62/111,149, filed on Feb. 3, 2015.

(51) Int. Cl.
| | |
|---|---|
| *C12N 15/11* | (2006.01) |
| *C12N 15/113* | (2010.01) |
| *A61K 31/343* | (2006.01) |
| *A61K 31/713* | (2006.01) |
| *A61K 31/409* | (2006.01) |
| *A61K 45/06* | (2006.01) |
| *A61K 9/00* | (2006.01) |

(52) U.S. Cl.
CPC ........ *C12N 15/1137* (2013.01); *A61K 9/0019* (2013.01); *A61K 31/343* (2013.01); *A61K 31/409* (2013.01); *A61K 31/713* (2013.01); *A61K 45/06* (2013.01); *C12Y 499/01001* (2013.01); *C12N 2310/14* (2013.01)

(58) Field of Classification Search
None
See application file for complete search history.

(56) References Cited

U.S. PATENT DOCUMENTS

| | | | | |
|---|---|---|---|---|
| 2007/0254350 | A1* | 11/2007 | Ferreira ................... | C12N 9/88 435/193 |
| 2008/0193499 | A1* | 8/2008 | Liu ......................... | A61K 31/00 424/423 |
| 2009/0005437 | A1* | 1/2009 | Gottlieb ................ | C07C 69/716 514/458 |
| 2011/0223105 | A1* | 9/2011 | Eriksson ................ | A61K 31/27 424/9.1 |

FOREIGN PATENT DOCUMENTS

WO    2014/182695    11/2014

OTHER PUBLICATIONS

Plosch et al, Mdr P-glycoproteins are Not Essential for Biliary Excretion of the Hydrophobic Heme Precursor Protoporphyrin in a Griseofulvin-Induced Mouse Model of Erythropoietic Protoporphyria, 2003, Hepatology, vol. 35, 2: 299-306.*
Teng et al, Silencing of ferrochelatase enhances 5-aminolevulinic acid-based fluorescence and photodynamic therapy efficacy, 2011, British Journal of Cancer, 104: 798-807.*
Kemmner et al, Silencing of human ferrochelatase causes abundant protoporphyrin-IX accumulation in colon cancer, FASEB Journal, 2008, 22: 500-509 (Year: 2008).*
Gilbert et al., Retinopathy of prematurity in middleincome countries. Lancet 350, pp. 12-14, (1997).
Faia et al., Retinopathy of prematurity care: screening to vitrectomy. Int Ophthalmol Clin. 51, pp. 1-16, (2011).
Yau et al. Global prevalence and major risk factors of diabetic retinopathy. Diabetes Care 35, pp. 556-564, (2012). PMCID: 3322721.
Fine et al., Age-related macular degeneration. New Engl J. Med 342, pp. 483-492, (2000).
Brown et al., The burden of age-related macular degeneration: a value-based medicine analysis. Trans Am Ophthalmol Soc 103, pp. 173-184; discussion pp. 184-176, (2005). PMCID: 1447589.
Prasad et al., Age-related macular degeneration: current and novel therapies. Maturitas 66, pp. 46-50, (2010).
Lux et al., Non-responders to bevacizumab (Avastin) therapy of choroidal neovascular lesions. Br J Ophthalmol 91, pp. 1318-1322, (2007). PMCID: 2000982.
Folk et al., Ranibizumab therapy for neovascular age-related macular degeneration. New Engl J Med 363, pp. 1648-1655, (2010).
De Matteis et al., Occurrence and biological properties of N-methyl protoporphyrin. Ann N Y Acad Sci 514, pp. 30-40, (1987).
Mitchell et al., Cost effectiveness of treatments for wet age-related macular degeneration. Pharmacoeconomics 29, pp. 107-131, (2011).
Hamza et al., One ring to rule them all: trafficking of heme and heme synthesis intermediates in the metazoans. Biochim Biophys Acta 1823, 1617-1632, (2012). PMCID: 3412874.
Chen et al., Ferrochelatase forms an oligomeric complex with mitoferrin-1 and Abcb10 for erythroid heme biosynthesis. Blood 116, pp. 628-630, (2010). PMCID: 3324294.v.
Koch et al., A. Crystal structure of protoporphyrinogen IX oxidase: a key enzyme in haem and chlorophyll biosynthesis. EMBO J 23, pp. 1720-1728, (2004). PMCID: 394243.
Smith et al., Heme proteins—diversity in structural characteristics, function, and folding. Proteins 78, pp. 2349-2368, (2010).
Sarkany et al., Recessive inheritance of erythropoietic protoporphyria with liver failure. Lancet 343, pp. 1394-1396, (1994).
Nakahashi et al., The molecular defect of ferrochelatase in a patient with erythropoietic protoporphyria. Proc Natl Acad Sci U S A 89, pp. 281-285, (1992). PMCID: 48220.
Tsuboi et al., Erythropoietic protoporphyria with eye complications. J Dermatol 34, pp. 790-794, (2007).
Magness et al., An exon 10 deletion in the mouse ferrochelatase gene has a dominant-negative effect and causes mild protoporphyria. Blood 100, pp. 1470-1477, (2002).

(Continued)

*Primary Examiner* — Ekaterina Poliakova-Georgantas

(57) ABSTRACT

Methods for treating angiogenesis-mediated diseases are disclosed. More particularly, the present disclosure relates to methods of inhibiting ferrochelatase as an antiangiogenic therapy.

11 Claims, 18 Drawing Sheets

(56) References Cited

OTHER PUBLICATIONS

Tutois et al., Erythropoietic protoporphyria in the house mouse. A recessive inherited ferrochelatase deficiency with anemia, photosensitivity, and liver disease. J Clin Invest 88, pp. 1730-1736, (1991). PMCID: 295715.

Lee et al., The first synthesis of the antiangiogenic homoisoflavanone, cremastranone. Org Biomol Chem 12, pp. 7673-7677, (2014). PMCID: 4167916.

Shim et al., Anti-angiogenic activity of a homoisoflavanone from Cremastra appendiculata. Planta Med 70, pp. 171-173, (2004).

Fukumura et al., Predominant role of endothelial nitric oxide synthase in vascular endothelial growth factorinduced angiogenesis and vascular permeability. Proc Natl Acad Sci U S A 98, pp. 2604-2609, (2001). PMCID: 30185.

Kim et al., Homoisoflavanone inhibits retinal neovascularization through cell cycle arrest with decrease of cdc2 expression. Biochem Biophys Res Commun 362, pp. 848-852, (2007).

Kim et al., Inhibition of choroidal neovascularization by homoisoflavanone, a new angiogenesis inhibitor. Mol Vis 14, pp. 556-561, (2008). PMCID: 2274926.

du Toit et al., Anti-inflammatory activity and QSAR studies of compounds isolated from *Hyacinthaceae* species and Tachiadenus longiflorus Griseb. (Gentianaceae). Bioorg Med Chem 13, pp. 2561-2568, (2005).

Hur et al., Homoisoflavanone inhibits UVB-induced skin inflammation through reduced cyclooxygenase-2 expression and NF-κB nuclear localization. J Dermatol Sci 59, pp. 163-169, (2010).

Lee et al., Homoisoflavanone prevents mast cell activation and allergic responses by inhibition of Syk signaling pathway. Allergy 69, pp. 453-462, (2014).

Basavarajappa, et al., Synthesis and mechanistic studies of a novel homoisoflavanone inhibitor of endothelial cell growth. vol. 10/1371(2014). PMCID: 3994091.

Bargagna-Mohan et al. The tumor inhibitor and antiangiogenic agent withaferin A targets the intermediate filament protein vimentin. Chem Biol 14, pp. 623-634, (2007). PMCID: 3228641.

Bhasin et al.,. Protoporphyrin-IX accumulation and cutaneous tumor regression in mice using a ferrochelatase inhibitor. Cancer Lett 187, pp. 9-16, (2002).

Auerbach et al., Angiogenesis assays: problems and pitfalls. Cancer Metastasis Rev 19, pp. 167-172, (2000).

Shi et al., Modulation of inhibition of ferrochelatase by N-methylprotoporphyrin. Biochem J 399, pp. 21-28, (2006). PMCID: 1570166.

Dailey et al., Mammalian ferrochelatase. Expression and characterization of normal and two human protoporphyric ferrochelatases. J Biol Chem 269, pp. 390-395, (1994).

Inoue et al., Photodynamic Therapy Involes an Antiangiogenic Mechanism and is Enhanced by Ferrochelatase Inhibitor in Urothelial Carcinoma, Cancer Science, Jun. 2013, vol. 104, pp. 765-772.

\* cited by examiner

| Cell line | GI50 value(μM) |
|---|---|
| HREC | 0.22 |
| HUVEC | 0.38 |
| 92-1 | 47 |
| Y79 | 10 |
| ARPE-19 | >250 |

INHIBITION OF FERROCHELATASE AS AN ANTIANGIOGENIC THERAPY

CROSS REFERENCE TO RELATED APPLICATIONS

This application claims priority to U.S. Provisional Application No. 62/111,149 filed on Feb. 3, 2015, which is hereby incorporated by reference in its entirety.

BACKGROUND OF THE DISCLOSURE

The field of the disclosure relates generally relates to methods for treating angiogenesis-mediated diseases. More particularly, the present disclosure relates to methods of inhibiting ferrochelatase as an antiangiogenic therapy.

Angiogenesis does not occur in the body, except during development and wound repair processes. However, during numerous pathological conditions, angiogenesis occurs, notably in ocular diseases such as retinopathy of prematurity (ROP), diabetic retinopathy (DR), and "wet" age-related macular degeneration (AMD). After pathological angiogenesis occurs, newly formed blood vessels are fragile, porous and not fully differentiated. The formation of such new blood vessels in the eye may lead to hemorrhage, rapid photoreceptor degeneration, and eventual fibrotic scarring, with rapid, permanent vision loss.

Clinical symptoms of DR are seen in 75% of diabetic patients, with 10% of them eventually developing visual impairment. DR is currently the leading cause of blindness among working age adults and accounts for 8% of the legal blindness in the United States. Additionally, almost 2 million Americans are affected by AMD. AMD has an estimated loss of productivity burden of 55.4 billion annually in the United States. Severely affected patients have a very poor quality of life, comparable to that of catastrophic stroke victims or advanced cancer patients in constant pain.

Established treatment modalities for AMD include thermal laser photocoagulation or photodynamic therapy in conjunction with verteporfin. More recently, anti-vascular endothelial growth factor therapies such as pegaptanib, ranibizumab, aflibercept, and bevacizumab have shown success in slowing and even reversing vision loss in some age-related macular degeneration patients. But the significant acute, systemic side effects (e.g., non-ocular hemorrhage, myocardial infarction, and stroke) indicate that these therapies can act outside the eye, even when delivered intravitreally. Blinding intraocular side effects are also possible and the long-term risks of these drugs are still unclear. Moreover, because they are biologics, the cost-benefit ratios of these drugs are unfavorable. For instance, ranibizumab costs approximately $2,000 per monthly dose, rendering these treatments unaffordable for many patients. Since recurrence after treatment cessation can also occur, treatment with drug combinations targeting different pathways that truly eradicate the disease has been touted as the future of therapy for this disease.

A similar situation exists for retinopathy of prematurity (ROP). Retinopathy of prematurity (ROP) is characterized by abnormal blood vessel growth in the neonatal retina. The disease develops in two stages. In the first, hyperoxic stage, from 22 to 30 weeks' gestational age, high oxygen levels (as experienced in the ventilated, extrauterine environment compared to in utero) lead to decreased VEGF production and subsequent cessation of vascularization. In the second phase, photoreceptors mature, and the avascular retina grows and becomes hypoxic, prompting production of VEGF. VEGF is essential for signaling normal vessel growth during development, but when aberrantly expressed at high levels, causes improper neovessel growth. Neovessels, extending into the vitreous, do not oxygenate the retina well and easily rupture, leading to retinal ganglion cell and photoreceptor loss, retinal detachment, and blindness.

In 2010, 12% of children in the United States were born prematurely, and 1.5% were very low birth weight (VLBW; <1500 g). Almost 70% of these VLBW infants were likely to develop ROP, which is caused by aberrant angiogenesis after exposure to postnatal hyperoxia. The disease is estimated to cause visual loss in 1300 children per year in the United States, and severe visual impairment in a further 500 children per year. Overall, between 6% and 18% of childhood blindness is attributable to ROP. Moreover, as more and more children survive premature birth in middle income countries due to improvements in neonatal intensive care, ROP is becoming more prevalent worldwide. Aside from the acute risk of blindness, in childhood and even as adults, ROP survivors are more likely than the general population to develop posterior segment pathology, retinal detachment, myopia, amblyopia, strabismus, early cataract, and glaucoma.

Although biologic treatments are effective for retinopathy of prematurity and show fewer side effects than surgical treatments, there remain significant concerns about lasting toxic or developmental effects in neonates, especially since these drugs can have systemic actions even when delivered locally. Accordingly, there is a critical unmet need for small molecules to treat ocular neovascularization disorders as well as other angiogenesis-mediated diseases, to complement the existing approaches and allow lower-dose, combination therapies.

BRIEF DESCRIPTION OF THE DISCLOSURE

The present disclosure is generally related to methods of inhibiting ferrochelatase as an antiangiogenic therapy. It has now been found that ferrochelatase (FECH) is a cellular target that can be blocked by small molecular compounds or genetic methods to assist in treating ocular neovascularization. Ferrochelatase inhibition by these methods inhibits angiogenesis, and thus has therapeutic potential for neovascular diseases, including, but not limited to, neovascular eye diseases.

Accordingly, in one aspect, the present disclosure is directed to a method of inhibiting angiogenesis in an individual in need thereof. The method comprises administering an agent that inhibits ferrochelatase to the individual.

In another aspect, the present disclosure is directed to a method of treating neovascular eye disease in an individual in need thereof. The method comprises administering an agent that inhibits ferrochelatase to the individual.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1A shows that griseofulvin treatment did not significantly change mouse weights during the experimental timecourse. FIG. 1B shows that griseofulvin increased liver weights with these treatments, confirming drug intake and systemic metabolism. The graphs show mean±SEM with n=6 mice for each group. ***, p<0.001.

FIG. 2A depicts the chemical structure of cremastranone (1) (top), and the anti-proliferative activity of cremastranone (bottom), shown as the 50% growth inhibitory concentration ($GI_{50}$) on human retinal endothelial cells (HRECs), human umbilical vein endothelial cells (HUVECs) and non-endothelial cells (uveal melanoma 92-1 and retinal pigment epithelium ARPE-19). FIG. 2B depicts structures of compounds used in photoaffinity chromatography as analyzed in Example 1. FIG. 2C depicts proteins pulled down with indicated reagents in photoaffinity chromatography separated on SDS-PAGE and silver stained. FIG. 2D is an immunoblot of pulled down proteins using antibody against ferrochelatase. FIG. 2E is an immunoblot of pulled down proteins from a competition assay with excess cremastranone isomer (4); quantification of band intensity is shown. FIG. 2F depicts a silver stained SDS-PAGE gel of recombinant human ferrochelatase protein pulled down using photoaffinity chromatography. FIG. 2G is an anti-FECH immunoblot of a similar pulldown experiment. All the gel and immunoblot images are representative from at least two independent experiments.

FIG. 3A shows 5-ALA induced protoporphyrin (PPIX) buildup in HRECs after cremastranone treatment. FIG. 3B shows partial rescue of HREC proliferation with 5-ALA, an inducer of heme biosynthesis. HRECs treated with DMSO only are shown as 100% proliferation control. FIG. 3C shows that cremastranone does not bind iron as determined in an iron chelation assay; EDTA and deferoxamine are positive controls. Representative figures from at least three independent experiments. Graphs show mean±SEM with n≥3. *, p<0.05; , p<0.01; *, p<0.001.

FIGS. 4A & 4B show that ferrochelatase can be knocked down using specific siRNAs as confirmed by immunoblot. FIG. 4C shows proliferation of HRECs monitored in presence or absence of FECH specific siRNA. FIG. 4D shows the time course of the effect of FECH siRNA on proliferation of HRECs. The % proliferation calculated is with respect to proliferation with negative control siRNA. FIG. 4E depicts a scratch-wound migration assay performed with or without FECH knock down in HRECs. FIG. 4F depicts the ability of HRECs to form tubes in vitro on Matrigel was monitored after knocking down FECH.

FIG. 7A depicts minimal effects on proliferation of ARPE-19 retinal pigment epithelial cells. FIG. 7B depicts minimal effects on proliferation of 92-1 uveal melanoma cells. FIG. 7C depicts minimal effects on proliferation of HUVECs. Graphs show mean±SEM with n>3. Representative figures from three experiments are shown.

FIG. 8A depicts whole mount staining of L-CNV mouse choroid stained with an antibody against Fech (red) and with agglutinin (green). FIG. 8B depicts immunostaining of sections of eyes from wet AMD or normal patients using an antibody against ferrochelatase (red). The nuclei of cells are stained blue with DAPI. FIG. 8C shows the quantification of the staining intensity of ferrochelatase in the subretinal region, where CNV occurs. FIG. 8D depicts whole mount staining of retina/choroid isolated from L-CNV mice treated with Fech specific siRNA. The choroidal vasculature was stained with agglutinin conjugated with Alexafluor 555 (red). FIG. 8E shows the quantification of the staining intensity of the choroidal vasculature as shown in FIG. 8D. *, p<0.05 for comparisons indicated.

FIG. 9D depicts a mouse choroidal sprouting assay used to further measure the antiangiogenic potential of griseofulvin in vitro. *, p<0.05; *, p<0.001; **, p<0.0001 relative to DMSO controls.

DETAILED DESCRIPTION

Figure 1A:
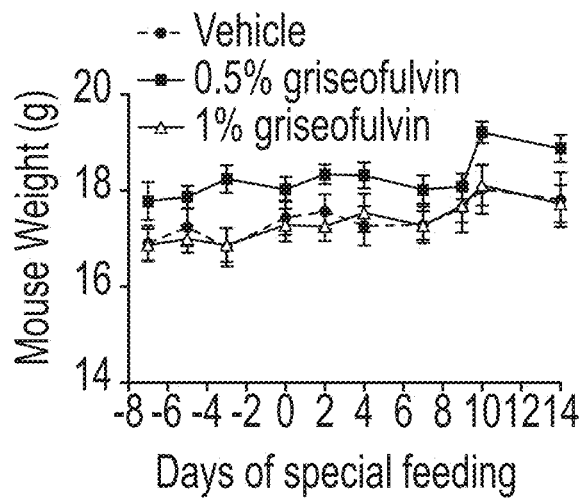
FIGS. 1A & 1B depict oral griseofulvin's systemic effects as analyzed in the Examples.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is generally related to methods of inhibiting ferrochelatase as an antiangiogenic therapy. Particularly, it has now been shown that angiogenesis is inhibited by blocking ferrochelatase. Inhibition of ferrochelatase has been shown to block ocular neovascularization, thereby treating neovascular eye diseases such as retinopathy of prematurity (ROP), proliferative diabetic retinopathy (PDR), and wet age-related macular degeneration (AMD).

Ferrochelatase (FECH) is a nuclear-encoded, mitochondrial inner membrane-associated enzyme responsible for the final step of heme biosynthesis. FECH catalyzes the insertion of ferrous ion ($Fe^{2+}$) into the center of protoporphyrin IX (PPIX) to complete the formation of heme. $Fe^{2+}$ is supplied by the inner membrane iron transporter mitoferrin stabilized by the channel ABCB10, while PPIX is produced by a cascade of porphyrin synthetic enzymes ending with protoporphyrinogen oxidase, which likely complexes with FECH to deliver PPIX. FECH-synthesized heme is then utilized as a cofactor by hemoproteins in the cell, including proteins important for angiogenesis such as nitric oxidase synthases (NOSs), mitochondrial Complex IV, hemoxygenase 1 (HO-1) and others.

In one aspect, the methods of the present disclosure generally include methods of inhibiting angiogenesis in an individual in need thereof by administering an agent that inhibits ferrochelatase to the individual. Exemplary angiogenesis and/or inflammation-mediated diseases capable of being treated with the methods of the present disclosure include neovascular diseases, non-ocular hemorrhage, myocardial infarction, stroke, cancer, atherosclerosis, ischaemic heart disease, coronary heart disease, peripheral arterial disease, wound healing disorders, and the like.

In some particular embodiments, the methods of the present disclosure include methods of treating neovascular eye disease in an individual in need thereof, the methods include administering an agent that inhibits ferrochelatase to the individual. Exemplary neovascular eye disease capable of being treated using the methods of the present disclosure include retinopathy of prematurity (ROP), "wet" age related macular degeneration (AMD), proliferative diabetic retinopathy (DR), pathological myopia, hypertensive retinopathy, occlusive vasculitis, polypoidal choroidal vasculopathy, uveitic macular edema, central retinal vein occlusion, branch retinal vein occlusion, corneal neovascularization, retinal neovascularization, ocular histoplasmosis, neovascular glaucoma, and the like.

Exemplary ferrochelatase inhibiting agents included in the compositions for use in the methods of the present disclosure include, for example, N-methylprotoporphryin (NMPP); the FDA-approved antifungal griseofulvin; antisense RNA, RNA silencing or RNA interference (RNAi) targeting ferrochelatase (FECH) RNA; CRISPR/Cas9-mediated or Zinc-finger nuclease-mediated genetic ablation of ferrochelatase (FECH) DNA, and combinations thereof.

Suitable dosage of the agent(s) for inhibiting ferrochelatase will depend upon a number of factors including, for example, age and weight of an individual, at least one precise condition requiring treatment, severity of a condition, nature of a composition, route of administration and combinations thereof. Ultimately, a suitable dosage can be readily determined by one skilled in the art such as, for example, a physician, a veterinarian, a scientist, and other medical and research professionals. For example, one skilled in the art can begin with a low dosage that can be increased until reaching the desired treatment outcome or result. Alternatively, one skilled in the art can begin with a high dosage that can be decreased until reaching a minimum dosage needed to achieve the desired treatment outcome or result.

By way of example only, when the ferrochelatase inhibiting agent is FECH siRNA, a suitable dosage may be from about 0.5 µM to about 10 µM, including from about 0.75 µM to about 5 µM, and in one particular embodiment, the dosage is about 1.25 µM. When the ferrochelatase inhibiting agent is griseofulvin, a suitable dosage may be from about 10 µM to about 500 µM, including from about 25 µM to about 250 µM, and including from about 50 µM to about 100 µM.

The ferrochelatase inhibiting agent(s) used in the methods of the disclosure can be administered as a pharmaceutical composition comprising the ferrochelatase inhibiting agent(s) of interest in combination with one or more pharmaceutically acceptable carriers. As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the active compound from one organ or portion of the body, to another organ or portion of the body. Each carrier must be "acceptable" in the sense of being compatible with the other components of the composition (e.g., agent for inhibiting ferrochelatase) and not injurious to the individual. Lyophilized compositions, which may be reconstituted and administered, are also within the scope of the present disclosure.

Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal, subretinal, subconjunctival), drop infusion preparations, or suppositories. For application by the ophthalmic mucous membrane route, they may be formulated as eye drops or eye ointments. These compositions can be prepared by conventional means, and, if desired, the active compound (i.e., ferrochelatase inhibiting agent) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the pharmaceutical compositions used in the methods of the present disclosure can further include additional known therapeutic agents, drugs, modifications of the synthetic compounds into prodrugs, and the like for alleviating, mediating, preventing, and treating the diseases, disorders, and conditions described herein.

In one aspect, the pharmaceutical compositions used in the methods of the present disclosure can further include anti-VEGF therapies, including, for example, anti-VEGF biologics such as ranibizumab, bevacizumab, aflibercept. In another aspect, the pharmaceutical compositions may include other therapeutics and biologics such as antisense RNA, RNA silencing or RNA interference (RNAi) of angiogenic factors, including ribozymes that target VEGF expression; FOVISTA® and other agents targeting platelet derived growth factor (PDGF); squalamine ((1S,2S,5S,7R,9R,10R, 11S,14R,15R)—N-{3-[(4-aminobutyl)amino]propyl}-9-hydroxy-2,15-dimethyl-14-[(2R,5R)-6-methyl-5-(sulfooxy) heptan-2-yl]tetracyclo[8.7.0.0^{2,7}.0^{11,15}]heptadecan-5-aminium); X-82 (Tyrogenix, Needham Heights, Mass.); PAN-90806 (PanOptica, Bernardsville, N.J.); TNP470 (Sigma-Aldrich, St. Louis, Mo.) and fumagillin (2E,4E,6E, 8E)-10-{[(3R,4S,5S,6R)-5-methoxy-4-[(2R)-2-methyl-3-(3-methylbut-2-enyl)oxiran-2-yl]-1-oxaspiro[2.5]octan-6-yl]oxy}-10-oxodeca-2,4,6,8-tetraenoic acid); protein kinase C inhibitors; inhibitors of VEGF receptor kinase; pigment epithelium derived factor (PEDF); endostatin; angiostatin; anecortave acetate; triamcinolone ((11β,16α)-9-Fluoro-11, 16,17,21-tetrahydroxypregna-1,4-diene-3,20-dione); verteporfin (3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.1$^{3,6}$.1$^{8,11}$.1$^{13,16}$.0$^{19,24}$]octacosa-1,3,5,7,9,11(27),12,14,16,18(25),19,21-dodecaen-9-yl]propanoic acid), porfimer sodium (photofrin), 5-aminolevulinic acid and other photosensitizers used with photodynamic therapy, and combinations thereof.

The pharmaceutical compositions including the ferrochelatase inhibiting agent and pharmaceutical carriers used in the methods of the present disclosure can be administered to a subset of individuals in need. As used herein, an "individual in need" refers to an individual at risk for or having angiogenesis and/or neovascular eye diseases. Additionally, an "individual in need" is also used herein to refer to an individual at risk for or diagnosed by a medical professional as having angiogenesis (e.g., myocardial infarction, stroke, cancer) and/or neovascular eye disease (e.g., ROP, PDR, AMD). As such, in some embodiments, the methods disclosed herein are directed to a subset of the general population such that, in these embodiments, not all of the general population may benefit from the methods. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein. In particular, the individual in need is a human. The individual in need can also be, for example, an animal such as, for example, a non-human primate, a mouse, a rat, a rabbit, a cow, a pig, and other types of research animals known to those skilled in the art.

Various functions and advantages of these and other embodiments of the present disclosure will be more fully understood from the examples shown below. The examples are intended to illustrate the benefits of the present disclosure, but do not exemplify the full scope of the disclosure.

EXAMPLES

Examples 1-4

Materials & Methods

EBM-2 and IMDM growth media were purchased from Lonza (Walkersville, Md., USA). HRECs and Attachment Factor were purchased from Cell Systems (Kirkland, Wash., USA). Clonetics® HUVECs were purchased from Lonza. All endothelial cells were used between passages 5 and 8. Endothelial Growth Medium (EGM-2) was prepared by mixing the contents of an EGM-2 "Bullet Kit" (Cat no. CC-4176) with Endothelial Basal Medium (EBM) (Lonza). 92-1 and ARPE-19 cells were grown in RPMI and DMEM media supplemented with 10% FBS and 1% penicillin-streptomycin as described in Basavarajappa et al. J Med Chem 58, pp. 5015-5027 (2015); identity was confirmed by STR profiling. Click-iT TUNEL Alexa Fluor-594 imaging assay kit (Cat no. C10246) was purchased from Molecular Probes (Eugene, Oreg., USA). Monoclonal antibody against α-tubulin (DM1A), protoporphyrin 5-aminolevulinic acid, hemin, griseofulvin and L-arginine were purchased from Sigma-Aldrich (St. Louis, Mo., USA). N-methyl protoporphyrin (NMPP) and the primary antibody against FECH (A-3) were obtained from Santa Cruz (Santa Cruz, Calif., USA). Antibodies against cleaved caspase 3 (5A1E) and eNOS (49G3) were from Cell Signaling (Danvers, Mass., USA). Secondary antibodies were from Thermo Fisher Scientific (Pittsburgh, Pa., USA). The TaqMan probes and 5'-ethynyl-2'-deoxyuridine (EdU) incorporation assay kit were procured from Life Technologies (Carlsbad, Calif., USA). AbD Serotec (Kidlington, UK) was the source of the alamarBlue, while BD Biosciences (San Jose, Calif., USA) supplied the Matrigel. 4,5-Diaminofluorescein diacetate (DAF-2 diacetate) was purchased from Cayman Chemicals (Ann Arbor, Mich., USA). ECL Prime Western Blotting Detection reagent was purchased from GE Healthcare (Buckinghamshire, UK).

Preparation of Photoaffinity Reagents

Synthesis and characterization of affinity reagents 2 and 3 are shown in WO2014182695A1, filed May 6, 2014, and incorporated by reference to the extent it is consistent herewith. Compounds 1 and 4 were synthesized as described in Lee et al., Org Biomol Chem 28, p. 28 (2014); Basavarajappa et al., PLoS One 9, e95694 (2014). For pulldowns, Neutravidin agarose beads (1 mL of 50% slurry) were washed three times in buffer A containing 25 mM Tris-HCl pH 7.4, 150 mM NaCl, 2.5 mM sodium pyrophosphate, 1 mM phenylmethylsulfonyl fluoride (PMSF), 0.1 mM sodium orthovanadate, 10 µg/mL aprotinin and 10 µg/mL leupeptin. The beads were then incubated with 100 µM affinity or control reagents 2 or 3 overnight at 4° C. with rotation. The beads were blocked using 1 mM biotin solution prepared in buffer A for 1 hour followed by incubation with 1 mg/mL cytochrome c solution for 1 hour at 4° C. The beads were then washed three times with buffer A and resuspended in 1 mL.

Photoaffinity Pull Down Experiments

Flash-frozen porcine brain (20 g) obtained from the Purdue-Indiana University School of Medicine Comparative Medicine Program was homogenized in 50 mL Buffer A using a tissue homogenizer. The homogenate was centrifuged at 2000×g for 5 minutes. The supernatant (51) was then dounced 50 times followed by 10-minute sonication with amplitude of 60% in cycles of 10-second sonication on and 40-second sonication off (Q125 from QSonica, Newtown, Conn., USA). The lysate was then centrifuged at 11,000×g for 30 minutes. The resulting supernatant (S2) and pellet (P2) fractions were both collected. The P2 pellet was resuspended in buffer B: 1% Triton X-100+buffer A and then dounced 25 times and centrifuged at 11,000×g for 30 minutes; supernatant (S3) was collected. Both S2 and S3 supernatants were equally divided and each fraction was incubated with 500 µL photoaffinity or control reagent conjugated to Neutravidin beads for 75 minutes at 4° C. with shaking.

The beads were collected by centrifugation at 500×g for 5 minutes, then resuspended in 1 mL of buffer B and irradiated with 365 nm UV light (Mercury bulb H44GS100 from Sylvania in a Black-Ray 100 A long-wave UV lamp) in a 60 mm Petri dish for 30 minutes at 4° C. The beads were then washed two times in buffer B, followed by three washes in high-salt buffer containing 25 mM Tris-HCl pH 7.4, 350 mM NaCl, 1% Triton X-100 and 1 mM PMSF. The beads were then washed again in salt-free buffer containing 25 mM Tris-HCl, 1% Triton X-100 and 1 mM PMSF. After 5 minutes incubation, the beads were collected and any residual liquid was removed using a Hamilton syringe. The Neutravidin beads were then boiled in 300 µL of 2×SDS-PAGE gel loading dye containing 30 µL of 2-mercaptoethanol for 10 minutes at 70° C. to release the bound proteins. After boiling, the contents were allowed to cool and after a quick spin the eluate was collected using a Hamilton syringe. The eluates were then analyzed in 4-20% gradient SDS-PAGE and the protein bands were visualized using silver staining. The protein bands pulled down specifically by photo-affinity reagent were excised from the silver stained SDS-PAGE gel and analyzed by mass spectrometry (IUSM Proteomics Core). Using Sequest™ algorithms and the swine database (UniProt), the identities of the pulled down proteins were confirmed (Table 1).

were made in Tris Buffered Saline-0.05% Tween-20 buffer containing 2% bovine serum albumin (BSA).

siRNA Knock Down of FECH in Cells

Cells were grown in 6-well plates until 80% confluency was achieved. Then, 7.5 µL of Lipofectamine RNAiMAX reagent (Life Technologies) mixed with 30 pmol of siRNAs was added to each well according to the protocol recom-

TABLE 1

Peptide mass fingerprinting analysis of proteins pulled down with a cremastranone affinity reagent from a porcine brain lysate

| Accession | Description | Score | Coverage | # Unique Peptides | # Peptides | # PSMs* |
|---|---|---|---|---|---|---|
| F1S1X4 | Ferrochelatase (Fragment) OS = Sus scrofa; GN = FECH; PE = 3; SV = 2 – [F1S1X4_PIG] | 62.55 | 34.4 | 9 | 9 | 59 |
| P00761 | Trypsin OS = Sus scrofa; PE = 1; SV = 1 – [TYRP_PIG] | 58.0 | 8.7 | 1 | 1 | 80 |
| F1RUV5 | Uncharacterized protein (Fragment) OS = Sus scrofa; GN = PC; PE = 4; SV = 2 – [F1RUV5_PIG] | 27.0 | 5.7 | 3 | 3 | 25 |
| I3LVD5 | Actin, cytoplasmic 1 OS = Sus scrofa; GN = ACTB; PE = 2; SV = 1 – [I3LVD5_PIG] | 26.9 | 14.7 | 3 | 3 | 16 |
| I3LNT6 | Uncharacterized protein OS = Sus scrofa; GN = KRT77; PE = 3; SV = 1 – [I3LNT6_PIG] | 21.7 | 3.8 | 2 | 2 | 24 |
| I3LLY8 | Uncharacterized protein OS = Sus scrofa; GN = KRT79; PE = 3; SV = 1 – [I3LLY8_PIG] | 18.8 | 4.5 | 1 | 2 | 7 |
| F1SGI7 | Uncharacterized protein (Fragment) OS = Sus scrofa; GN = LOC100525745; PE = 3; SV = 2 – [F1SGI7_PIG] | 18.2 | 3.9 | 1 | 2 | 5 |
| F1SHC1 | Uncharacterized protein OS = Sus scrofa; GN = LOC100127131; PE = 3; SV = 1 – [F1SCH1_PIG] | 12.8 | 5.6 | 2 | 2 | 5 |

For competition experiments, S2 and S3 supernatants were incubated with affinity reagent-Neutravidin beads in the presence of 1 mM of cremastranone isomer SH-11052 (4) (Basavarajappa et al., PLoS One 9, e95694 (2014)) and then processed as described above.

Recombinant FECH

Recombinant human FECH protein was purified as described in Dailey et al., J Biol Chem 269, pp. 390-395 (1994). Briefly, Escherichia coli JM109 cells transformed with plasmid pHDTF20 encoding recombinant human FECH were grown in Circlegrow medium containing 100 µg/mL ampicillin for 20 hours at 30° C. The cells were harvested and resuspended in solubilization buffer (50 mM Tris-MOPS pH 8.0, 1% sodium deoxycholate, 100 mM KCl and 1 mM PMSF). The cell suspension was sonicated and then ultracentrifuged at 45000×g for 30 minutes. The supernatant was subjected to cobalt-affinity chromatography and the column was washed with solubilization buffer containing 20 mM imidazole. The protein was eluted with 250 mM imidazole in solubilization buffer. The protein eluate was then dialyzed in solubilization buffer containing 10% glycerol before storage at 4° C. Recombinant protein (200 µg) was used in pulldown experiments as above.

Immunoblot Assay

Immunoblots were performed as described Basavarajappa et al., PLoS One 9, e95694 (2014). Briefly, cell lysates were prepared by incubating the cells for 10 minutes at 4° C. in NP-40 lysis buffer (25 mM HEPES pH 7.6, 150 mM NaCl, 1% NP-40, 10% glycerol, 1 mM sodium orthovanadate, 10 mM NaF, 1 mM PMSF, 10 µg/mL aprotinin, 1 µM pepstatin, 1 µM leupeptin) and then centrifuged at 12,000×g for 15 minutes at 4° C. Supernatant was collected and protein concentration was determined using a Bradford assay. Equal amounts of total protein (40 µg) from each sample were resolved by 10% SDS-PAGE and then transferred onto PVDF membranes. Proteins were immunoblotted with antibodies against FECH (1:1000 dilution), α-Tubulin (1:1000 dilution) and eNOS (1:500 dilution). All of the dilutions mended by the manufacturer. For FECH knockdown, 15 pmol each of two siRNAs (SASI_Hs01_00052189 and SASI_Hs01_00052190; Sigma) were used and for negative control, MISSION® siRNA Universal negative control was used. Fresh EGM-2 medium was added to the plate 24 hours after transfection and cells were used 48 hours after transfection for further experiments except for the proliferation time course, for which 24 hours after transfection the cells were trypsinized and seeded in a 96-well plate.

Cell Proliferation Assay

Proliferation of cells was monitored as described in Basavarajappa et al., PLoS One 9 (2014). Briefly, after FECH knockdown 2,500 cells in 100 µL of growth medium were plated in each well of 96-well clear-bottom black plates and incubated for 24 hours. Then, compound/DMSO vehicle (final DMSO concentration of 1%) were added and the plates were incubated for 44 hours in 100 µL media at 37° C. and 5% $CO_2$. Then, 11.1 µL of alamarBlue reagent was added to each well of the plate and 4 hours later fluorescence readings were taken at excitation and emission wavelengths of 560 nm and 590 nm respectively using a Synergy H1 plate reader (BioTek, Winooski, Vt., USA). The concentration ranges of griseofulvin and NMPP used were 0.5 nM-500 µM and 0.1 nM-100 µM respectively.

Migration Assay

The migration of HRECs was monitored as described in Basavarajappa et al., PLoS One 9, e95694 (2014). Briefly, HRECs were grown until confluency in 6-well plates and then serum starved overnight in EBM-2 medium. Then, using a sterile 10 µL tip, a scratch was introduced in each well and fresh EGM-2 medium containing DMSO or different concentrations of compounds was added to the wells. For knockdown experiments, the scratch was introduced 48 hours after transfection and fresh medium was added to the wells. Photographs of the wells were taken at different time points to measure the number of migrated cells into the scratched area.

In Vitro Matrigel Tube Formation Assay

The ability of HRECs to form tubes in vitro was monitored as described in Basavarajappa et al., J Med Chem 58, pp. 5015-5027 (2015). Briefly, HRECs were treated with the indicated concentrations of compounds or DMSO or siRNAs for 48 hours and then 15,000 HRECs in 100 µL of EGM-2 medium containing siRNAs, DMSO or compounds were added to each well of a 96-well plate that was pre-coated with 50 µL of Matrigel basement membrane. Photographs of each well at different time points were taken to measure the tube formation using the Angiogenesis Analyzer plugin in ImageJ software (v.1.48).

PPIX Build-Up Assay

HRECs were grown in a 6-well plate until confluent. Then, cells were serum starved overnight in EBM-2 medium. Fresh EGM-2 medium containing DMSO or compounds was added to cells, and they were incubated at 37° C. for 1 hour followed by addition of 1 mM 5-ALA to increase flux through the heme biosynthetic pathway. After 3 hours of incubation in the dark at 37° C., the cells were trypsinized and lysed in buffer containing 25 mM HEPES-NaOH pH 7.4, 150 mM NaCl, 1% NP-40, 10% glycerol and 1 mM PMSF. The cell lysates were incubated in the dark at 4° C. for 20 minutes on a shaker and centrifuged at 12000×g for 15 minutes. Supernatants were collected for analysis. In a 384-well black plate, 20 µL of supernatant was mixed with 20 µL of 1:1 solution of 2 M perchloric acid and methanol. After 5 minutes of incubation, fluorescence readings were taken at excitation and emission wavelengths of 407 nm and 610 nm using the Synergy plate reader.

Iron Chelation

Compound or DMSO (1 µL) was incubated with 2.5 mM freshly prepared ferrous ammonium sulphate in a final volume of 100 µL for 5 minutes at 37° C. Then, 100 µL of 2.5 mM ferrozine solution was added to the wells and spectrophotometric readings were taken at 562 nm using the Synergy plate reader. Decrease in absorbance readings at 562 nm represents iron chelation.

Apoptosis Assays

Caspase-3 Immunofluorescence Assay:

The assay was performed as described in Basavarajappa et al., PLoS One 9, e95694 (2014). Briefly, cells were plated on coated coverslips and incubated in EGM-2 medium overnight before treating with siRNAs. After 24 hours of transfection, the cells were fixed in 4% paraformaldehyde and permeabilized using 0.5% Triton X-100 solution prepared in PBS. The cells were then incubated with cleaved caspase-3 (D175) antibody (1:200 dilution) overnight at 4° C. Dylight 488 conjugated goat anti-rabbit secondary antibody (1:400) was used to probe the cleaved caspase-3 antibody. The coverslips were mounted using Vectashield mounting medium containing DAPI for nuclear staining. The cells were imaged using an LSM 700 confocal microscope.

TUNEL Assay:

The assay was carried out as described in Basavarajappa et al., J Med Chem 58, pp. 5015-5027 (2015). Briefly, cells (25,000 per coverslip) were seeded on coverslips and 24 hours later the cells were transfected with siRNAs for 24 hours. Cells were then fixed in 4% paraformaldehyde for 20 minutes and permeabilized using 0.25% Triton X-100 prepared in PBS. Then, apoptotic cells were visualized using the Click-iT TUNEL assay kit as per the manufacturer's instructions, with DAPI counter-stain. The percentage of apoptotic cells was counted on three low-power fields per coverslip using ImageJ software and analysed using GraphPad Prism software (v. 6.0).

Animals

All animal experiments were approved by the Indiana University School of Medicine Institutional Animal Care and Use Committee and followed the guidelines of the Association for Research in Vision and Ophthalmology Statement for the Use of Animals in Ophthalmic and Visual Research. Wild-type female C57BL/6J mice, 6-8 weeks of age or timed pregnancies, were purchased from Jackson Laboratory (Bar Harbor, Me.) and housed under standard conditions. Mice were anesthetized for all procedures by intraperitoneal injections of 17.5 mg/kg ketamine hydrochloride and 2.5 mg/kg xylazine.

Choroidal Sprouting Assay

To assess choroidal sprouting, pieces of choroid-sclera dissected from euthanized mouse eyes were embedded in Matrigel and grown in EGM-2 medium plus antibiotics for 72 hours to allow sprouting to initiate. The indicated concentrations of griseofulvin (in DMSO, final DMSO concentration 1%) were added and growth allowed to proceed for 48 hours. Images were taken and growth quantified by measuring distance from the edge of the choroidal piece to the growth front in 4 directions per sample.

L-CNV Model

L-CNV was generated as described in Poor et al., Invest Ophthalmol Vis Sci 55, pp. 6525-6534 (2014); Sulaiman et al., J Ocul Pharmacol Ther 31, pp. 447-454 (2015). Briefly, eyes were dilated using 1% tropicamide, then underwent laser treatment using 50 µm spot size, 50 ms duration, and 250 mW pulses of an ophthalmic argon green laser, wavelength 532 nm, coupled to a slit lamp. Where indicated, intravitreal injections of PBS vehicle, siRNA (1.25 µM final intravitreal concentrations) or griseofulvin (50 µM, 100 µM, final intravitreal concentrations) were given in a 0.5 µL volume at time of laser treatment. Eyes were numbed with tetracaine solution before the injection, and triple antibiotic ointment was used immediately after the injection to prevent infection. A masked researcher undertook imaging and analysis to avoid bias. One week after laser treatment, mice underwent optical coherence tomography using a Micron III imager (Phoenix Research Labs, Pleasanton, Calif., USA) and CNV lesions were quantified as ellipsoids. Two weeks after laser treatment, eyes were enucleated and fixed, choroidal flatmounts prepared, and vasculature stained with rhodamine labeled *Ricinus communis* agglutinin I (Vector Labs, Burlingame, Calif., USA), followed by confocal Z-stack imaging (LSM 700, Zeiss, Thornwood, N.Y., USA) to estimate lesion volume.

Griseofulvin Feeding

Figure 1B:
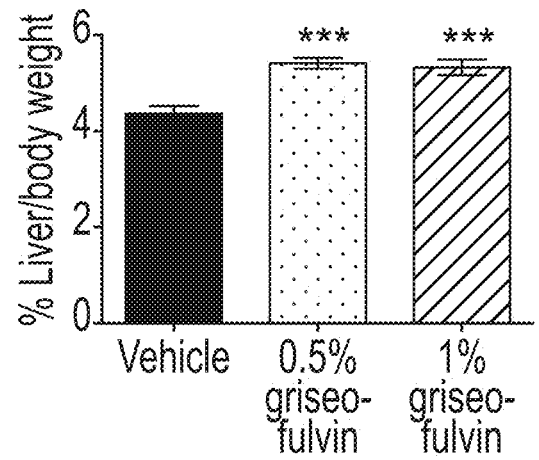

Mice were fed griseofulvin for a total of 3 weeks, with chow changed every 2-3 days. Standard mouse chow (5 g/mouse/day) was mixed in water (2.2 mL $H_2O$/gram chow), soaked for 15 minutes, then mashed. Griseofulvin doses were prepared at 0.0% (control), 0.5%, and 1.0% with 0.0 g, 0.5 g, and 1.0 g griseofulvin: 10 mL corn oil: 100 g mouse chow ratio, respectively. Both 0.5% and 1.0% doses were expected to substantially inhibit FECH and induce a protoporphyria-like phenotype. The corn oil solutions and mouse chow mixture were manually mixed thoroughly for 10 minutes. During treatment, the mice were examined and weighed 3 times/week (FIG. 1A). On Day 8, mice underwent L-CNV as above, and were imaged by OCT at Day 15 and Day 22, at which time they were euthanized. The eyes were enucleated and flatmounts prepared as above. The livers were dissected out and weighed (FIG. 1B).

Immunostaining

Human donor eyes were obtained from the National Disease Research Interchange with full ethical approval for use in research. Mouse eyes were post induced laser-CNV for 14 days. The eyes were enucleated and fixed in 4% paraformaldehyde/PBS overnight. The anterior segment, lens, and vitreous were removed and the posterior eye cups were prepared for standard paraffin sections or retinal flat mounts. Deparaffinized sections were treated with rodent deblocker (Biocare Medical) for antigen retrieval. The sections or flat mounts were washed with PBS then permeabilized with 0.3% Triton X-100 and nonspecific binding blocked by 10% normal goat serum plus 1% BSA in PBS. They then received primary antibody (polyclonal anti-FECH at 1:500 (C20, Santa Cruz) for 16 hours at 4° C. After primary incubation, tissues were washed and incubated for 1.5 hours at room temperature with secondary antibody (Cy3 conjugated goat anti-rabbit IgG, 1:600) at 4° C. with 0.1% Triton X-100. A vascular specific dye (*Ricinus Communis* Agglutinin I; Vector Laboratories, Inc.) conjugated to AlexaFluor 488 was used to label retinal vasculature. This was incubated for 30 minutes at room temperature in 1:400 of 10 mM HEPES plus 150 mM NaCl and 0.1% Tween-20. After washing, specimens were mounted in aqueous mounting medium (VectaShield; Vector Laboratories, Inc.) and coverslipped for observation by confocal microscopy. All microscopic images were acquired with identical exposure settings.

Statistical Analyses

Both in vitro and in vivo data were analyzed using Student's t-test or one-way ANOVA with Dunnett's or Tukey's post hoc tests for comparisons between the groups as appropriate. The choroidal sprouting assay was analyzed by two-way ANOVA with Dunnett's post hoc tests. All analyses were performed using GraphPad Prism 6 software. P-values of <0.05 were considered significant in all tests.

Example 1

In this Example, protein modulators of angiogenesis were identified.

Figure 2A:
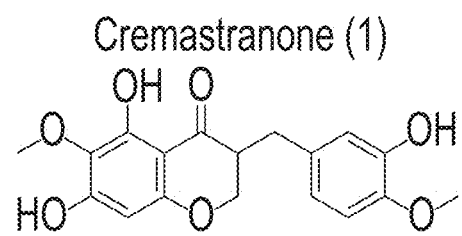
FIGS. 2A-2G depict ferrochelatase as a target of the antiangiogenic natural product, cremastranone.
Figure 2B:
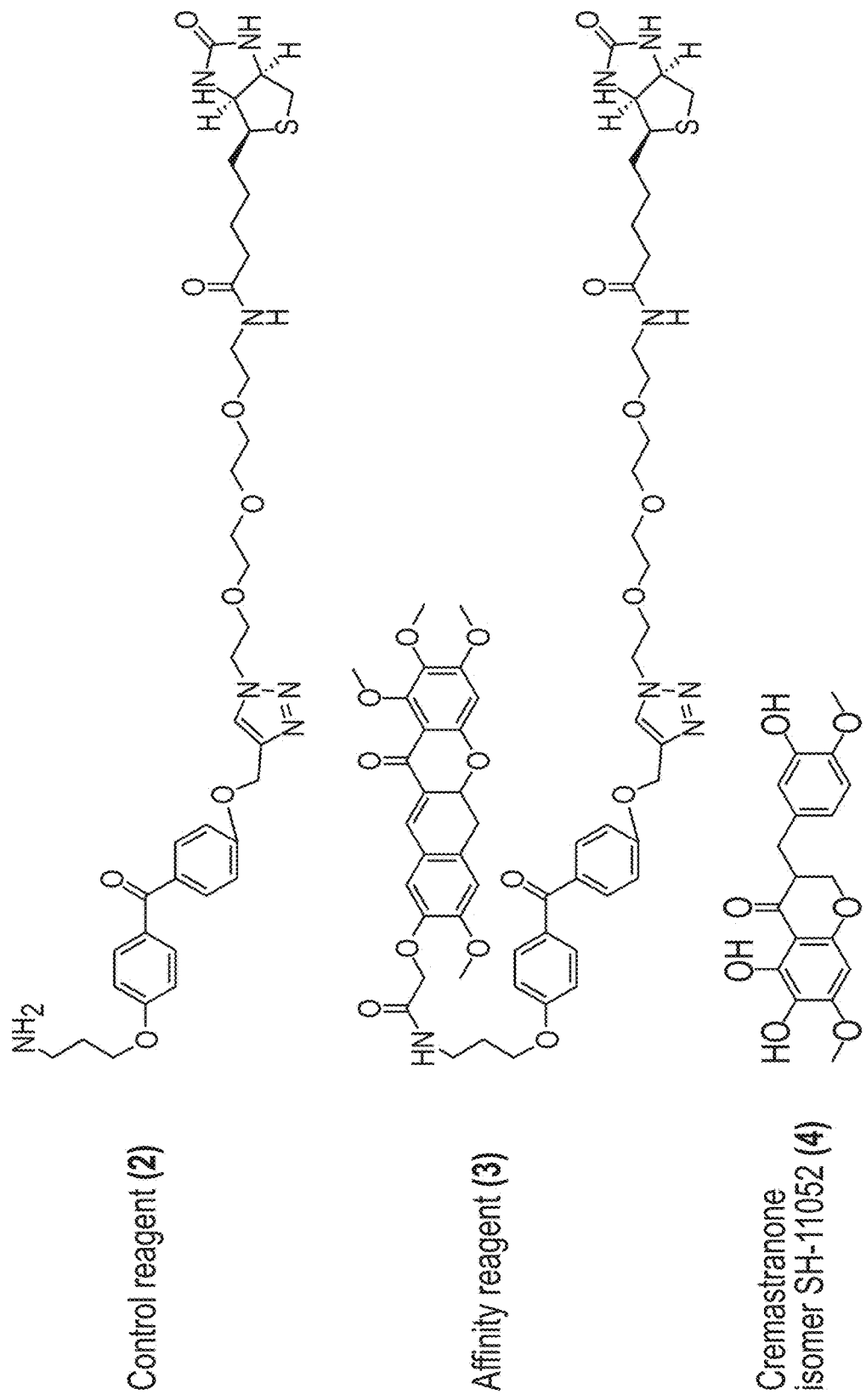
Figures 2C, 2D:
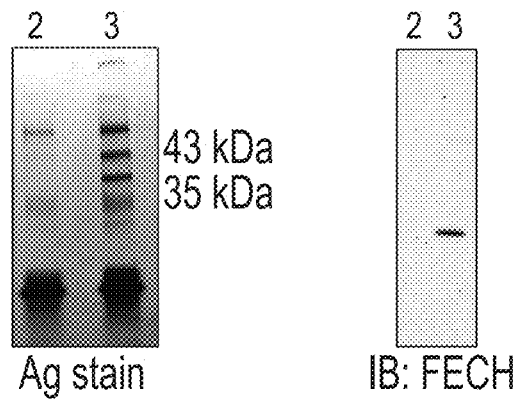
Figures 2E, 2F, 2G:
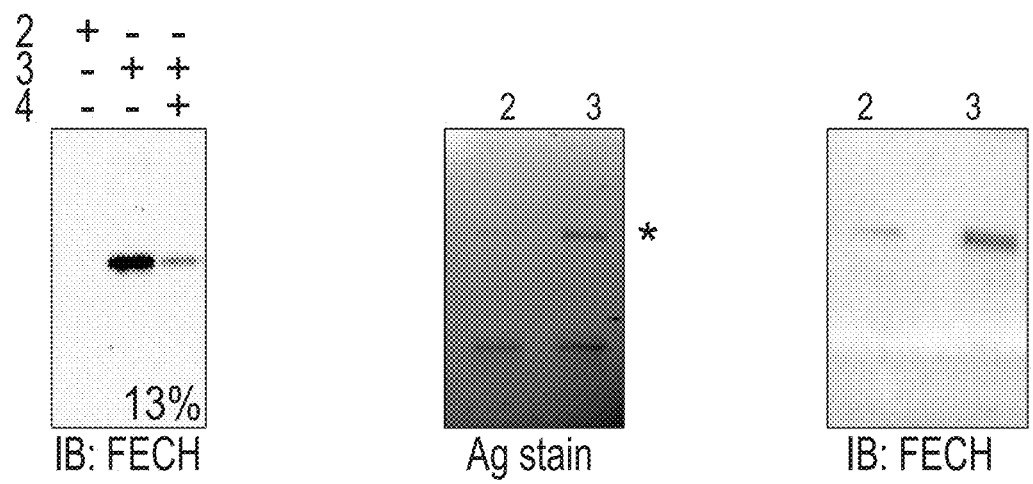

Photoaffinity chromatography was used to search for targets of the naturally occurring antiangiogenic compound, cremastranone (FIG. 2A), which has selective antiproliferative effects on endothelial cells. Protein binding partners of cremastranone were pulled down from a tissue lysate using immobilized affinity reagent, but not a negative control reagent (FIG. 2B). One of the two pulled down proteins was identified using peptide mass fingerprinting as ferrochelatase (FIG. 2C and Table 1) Immunoblot of eluates from photoaffinity pull down experiments confirmed the identity of the pulled down protein using an antibody against ferrochelatase (FIG. 2D). In order to confirm specificity of binding between cremastranone and pulled down proteins, affinity reagent was incubated with tissue proteins in the presence of excess active cremastranone isomer (FIG. 2B). Under this condition, the binding of ferrochelatase to affinity reagent was markedly (87%) decreased, indicating competition for binding to ferrochelatase between the cremastranone isomer and the affinity reagent (FIG. 2E).

Figure 3A:
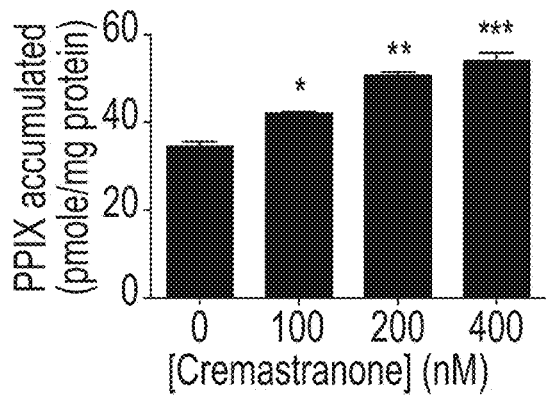
FIGS. 3A-3C depict validation of cremastranone's inhibition of FECH.
Figure 3B:
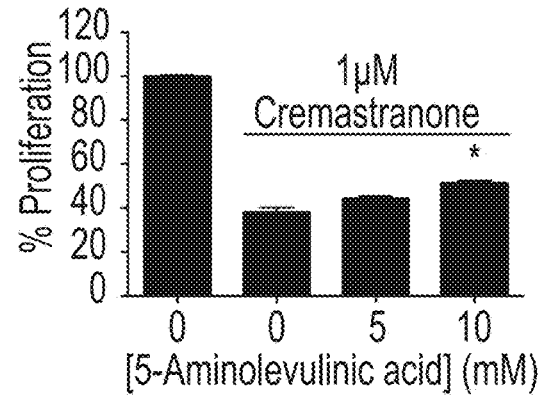
Figure 3C:
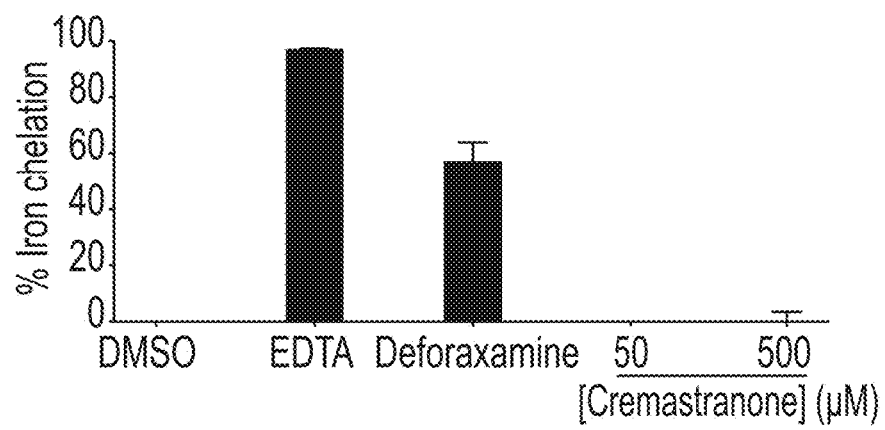

Recombinant FECH also interacted with the affinity reagent (FIGS. 2F & 2G), indicating that the interaction does not require eukaryotic accessory proteins. Moreover, cremastranone treatment of human retinal endothelial cells (HRECs) caused a dose-dependent buildup of PPIX (FIG. 3A), indicative of FECH inhibition, and addition of excess 5-aminolevulinic acid (5-ALA; the first precursor compound in the heme biosynthetic pathway that promotes increased heme production) partially rescued cremastranone's antiproliferative effects on HRECs (FIG. 3B). Cremastranone did not chelate iron, suggesting that it does not act indirectly on FECH by sequestering $Fe^{2+}$ substrate (FIG. 3C). The FECH pathway, therefore, is targeted by a known antiangiogenic compound indicating that this protein and pathway are important for angiogenesis.

Ferrochelatase is Required for Angiogenesis In Vitro

Figure 4A:
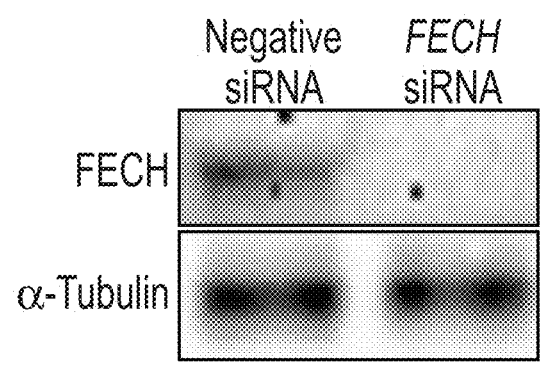
FIGS. 4A-4F depict ferrochelatase as an essential protein for angiogenesis in vitro.
Figure 4B:
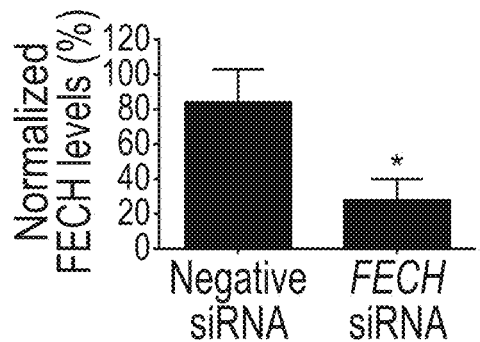
Figure 4C:
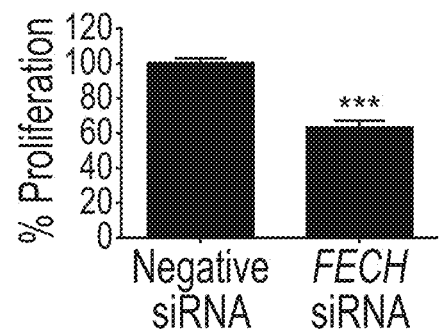
Figure 4D:
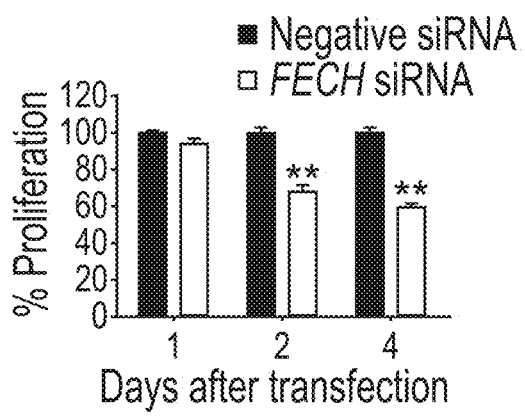
Figure 4E:
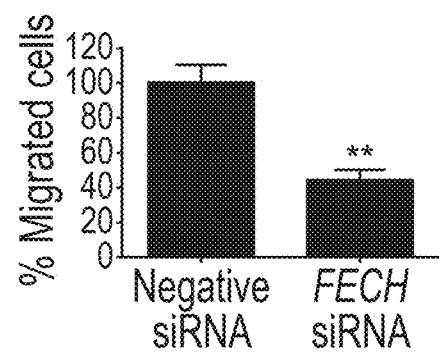
Figure 4F:
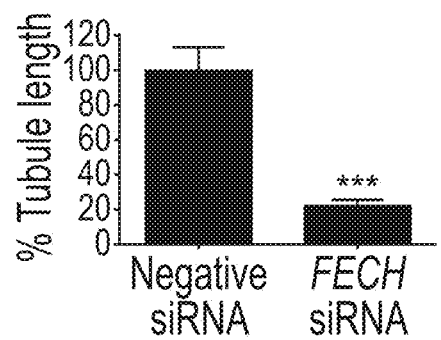

Further, the role of FECH in angiogenesis was evaluated. To determine if FECH plays a key role in angiogenesis, FECH was knocked down in HRECs using siRNA (FIGS. 4A & 4B) and key angiogenic properties of HRECs were monitored in vitro. FECH knockdown significantly reduced the proliferation of HRECs (FIGS. 4C & 4D). There was also a significant decrease in migration of HRECs treated with FECH siRNA in a scratch wound assay (FIG. 4E). Further, knocking down FECH in HRECs completely abolished the tube formation ability of HRECs as monitored by Matrigel assay (FIG. 4F).

Example 2

In this Example, a known pharmacological inhibitor of ferrochelatase was analyzed for its antiangiogenic properties in vitro.

Figure 5A:
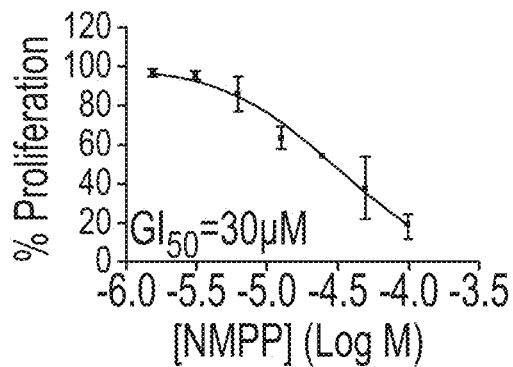
FIGS. 5A-5C depict the effect of NMPP, a specific inhibitor of ferrochelatase activity, on in vitro proliferation (FIG. 5A), migration (FIG. 5B) and tube formation ability (FIG. 5C) of HRECs. Graphs show mean±SEM, n≥3 samples. Representative results from at least 3 independent experiments. *, p<0.05; , p<0.01; *, p<0.001 relative to negative siRNA or DMSO controls.
Figure 5B:
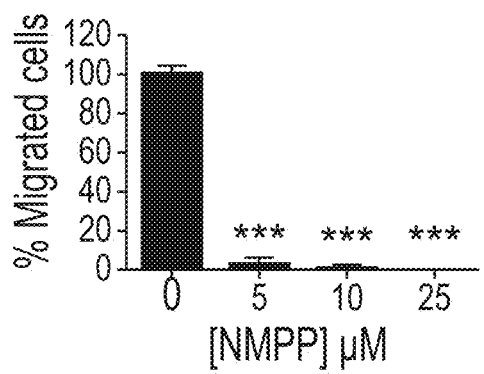
Figure 5C:
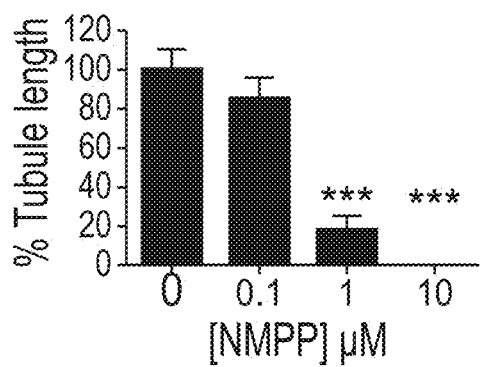
Figure 6:
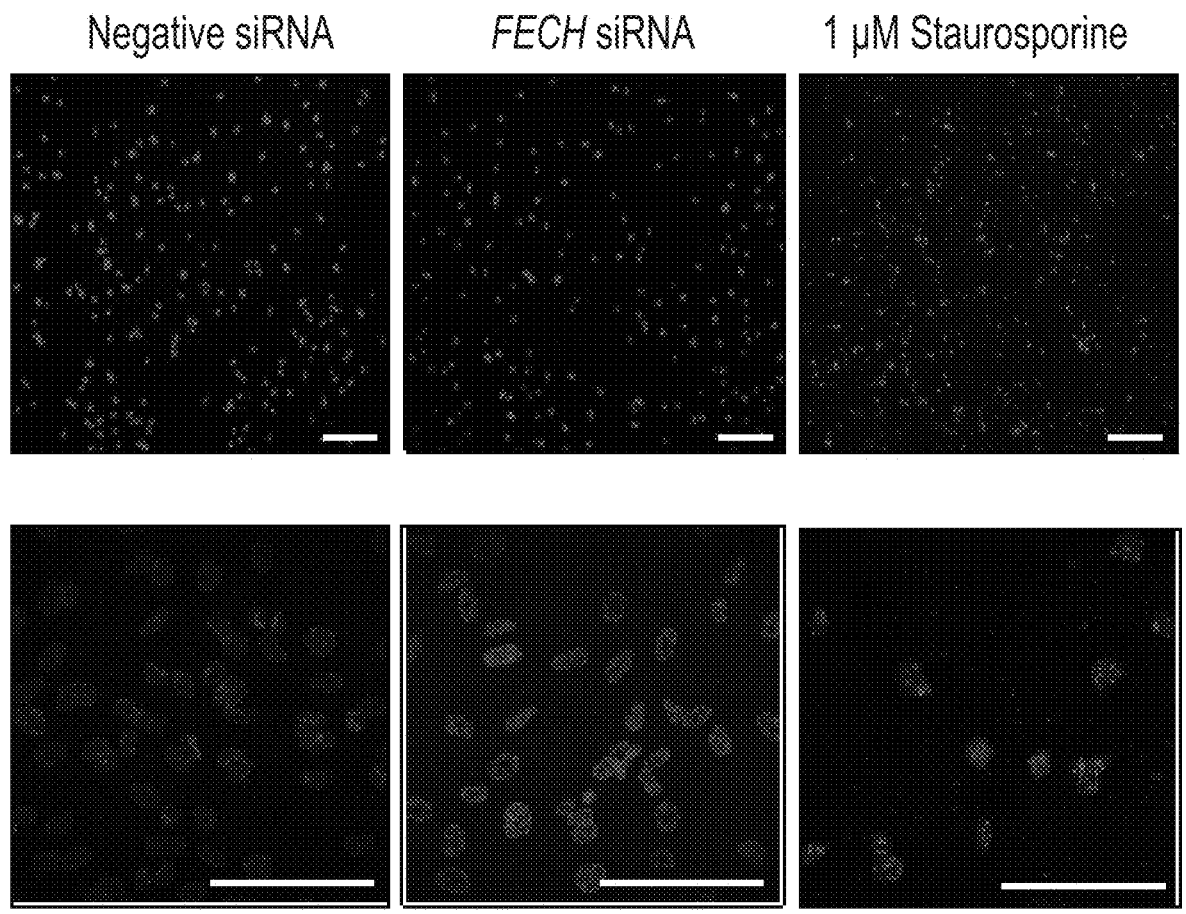
FIG. 6 shows that FECH knockdown did not induce apoptosis, as assessed by TUNEL (red). Staurosporine was a positive control.
Figure 7A:
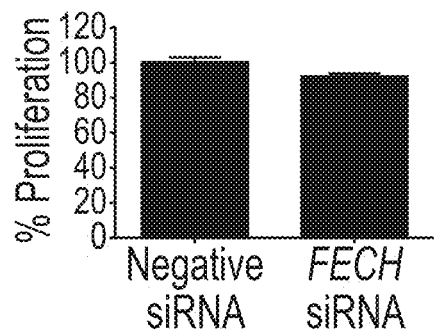
FIGS. 7A-7C depict FECH knockdown effects on proliferation of other cell types.
Figure 7B:
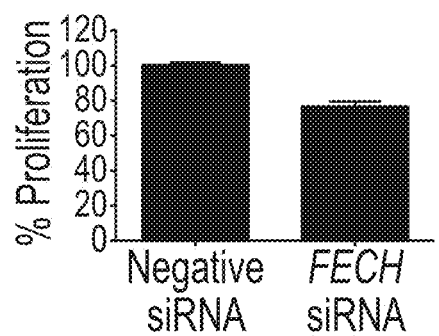
Figure 7C:
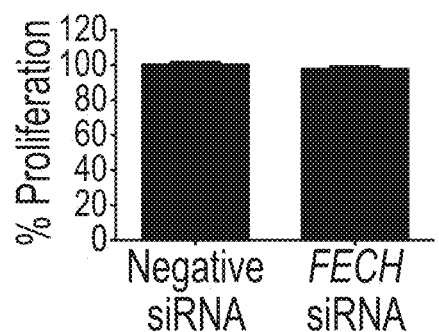

N-methyl protoporphyrin (NMPP), a competitive inhibitor of FECH activity, also inhibited proliferation, migration and tube formation ability of HRECs in vitro (FIGS. 5A-5C). However, despite these potent antiproliferative effects, FECH knockdown and low-dose chemical inhibition were not associated with increased apoptosis of these cells (FIG. 6), indicating a cytostatic rather than cytotoxic effect. Moreover, FECH knockdown did not inhibit proliferation of non-endothelial ocular cell lines 92-1 and ARPE-19 as well as macrovascular endothelial cell HUVECs (FIGS. 7A-7C), indicating that FECH inhibition is not associated with ocular cytotoxicity. Together, these experiments confirmed that ferrochelatase function is required for angiogenesis in vitro.

Example 3

In this Example, the association of ferrochelatase with neovascularization in vivo was evaluated.

Figure 8A:
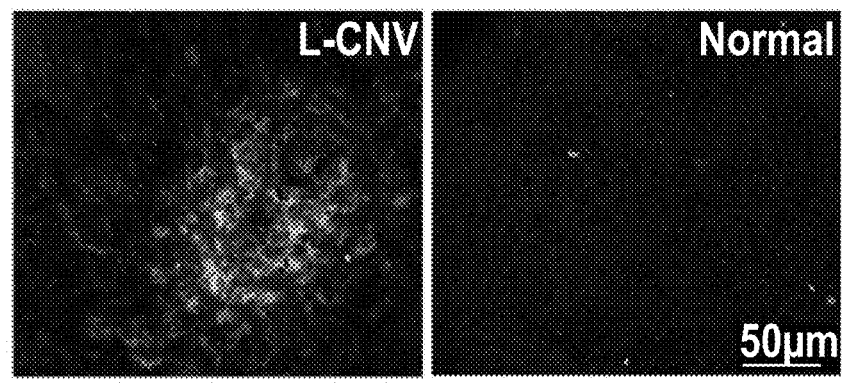
FIGS. 8A-8E show ferrochelatase as an essential protein for angiogenesis in vivo.
Figure 8B:
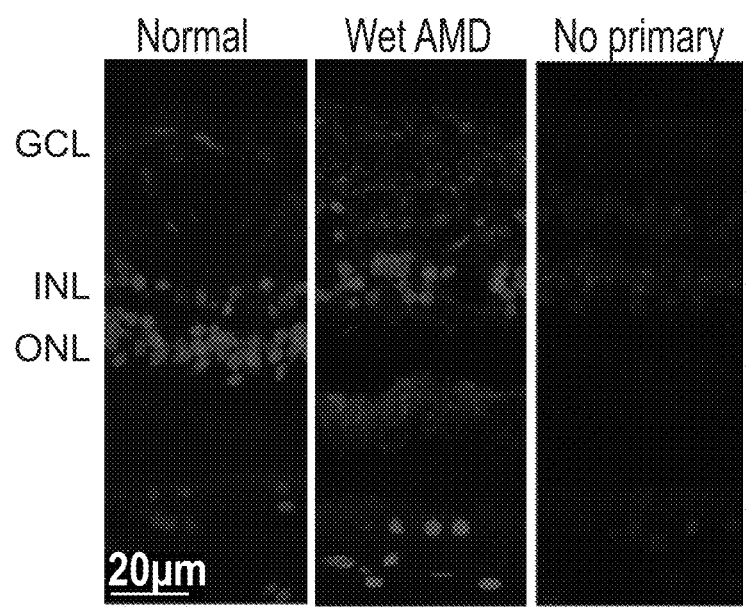
Figure 8C:
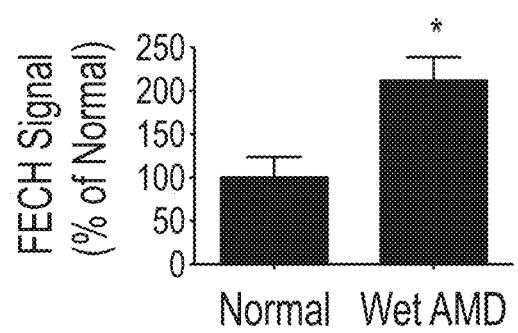

A mouse model of laser-induced choroidal neovascularization (L-CNV) was used. This widely used model recapitulates some of the features of wet AMD. FECH was overexpressed in and around lesions during neovascularization in this model (FIG. 8A). More importantly, FECH expression was seen throughout the retinas of human wet AMD patients analyzed postmortem (FIG. 8B). In the choroid, the source of neovascularization in wet AMD, expression was significantly increased compared to healthy eyes (FIG. 8C).

Figure 8D:
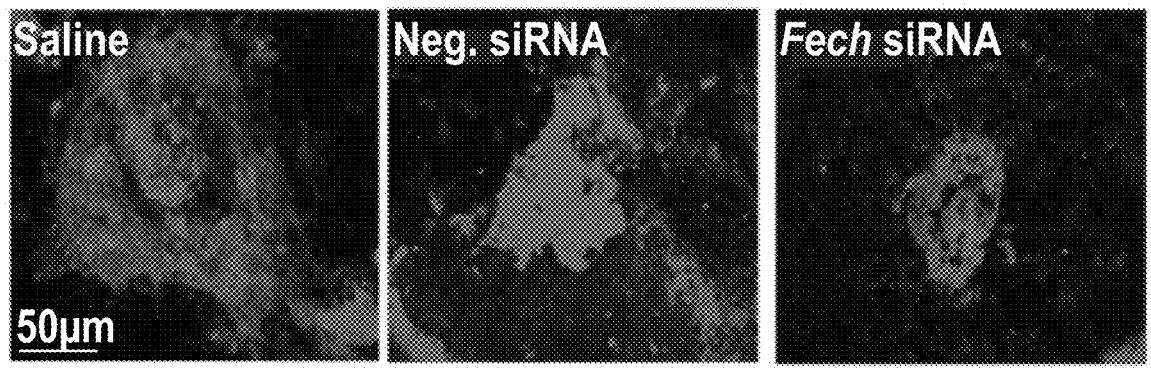
Figure 8E:
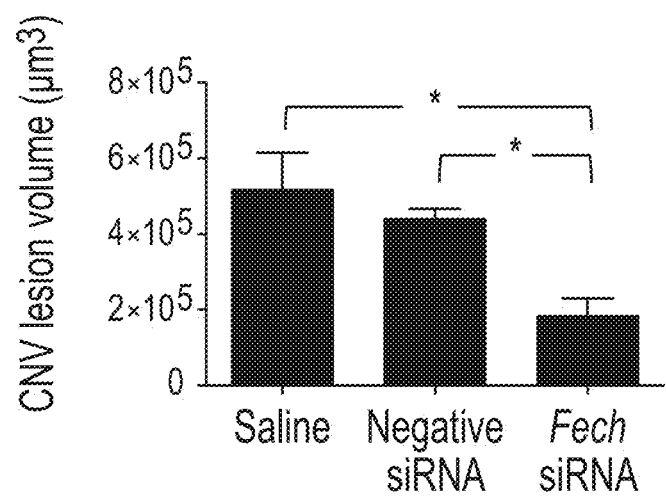

Since FECH upregulation suggested a role for this protein in neovascularization in the living eye, the effect of decreased FECH in this process was evaluated. When L-CNV mice were treated intravitreally with 1-BCH-specific siRNA, there was a significant decrease in choroidal neovascularization as compared with both saline treated control mice, as well as control non-coding siRNA treated mice (FIGS. 8D & 8E). These in vivo experiments confirm the clinical relevance of FECH in neovascularization, and the value of targeting this enzyme to block this process.

Example 4

In this Example, ferrochelatase-targeting therapy was evaluated for its ability to treat neovascularization.

Figure 9A:
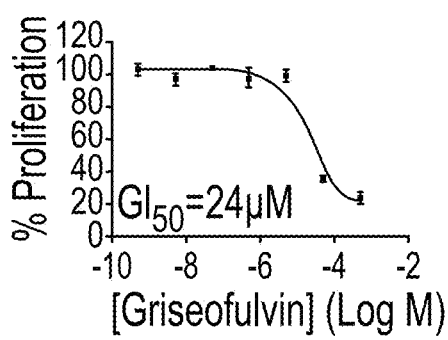
FIGS. 9A-9D depict chemical inhibition of ferrochelatase on angiogenesis in vitro. The effect of griseofulvin, a FDA-approved drug that inhibits ferrochelatase activity, on proliferation (FIG. 9A), migration (FIG. 9B), and tube formation ability (FIG. 9C) of HRECs was monitored in vitro.
Figure 9B:
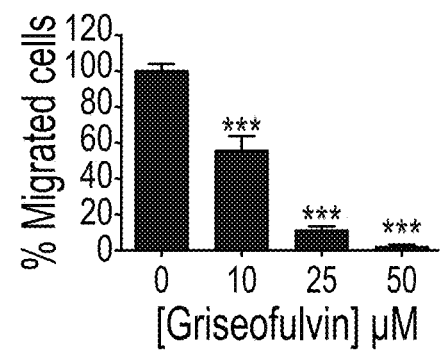
Figure 9C:
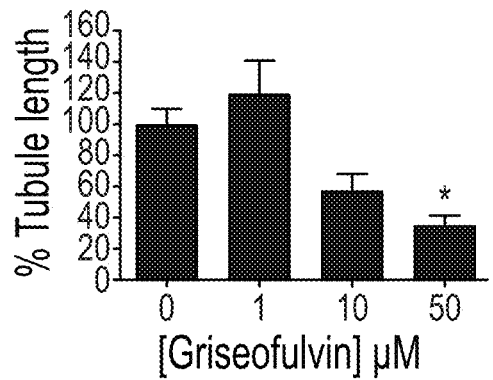
Figure 9D:
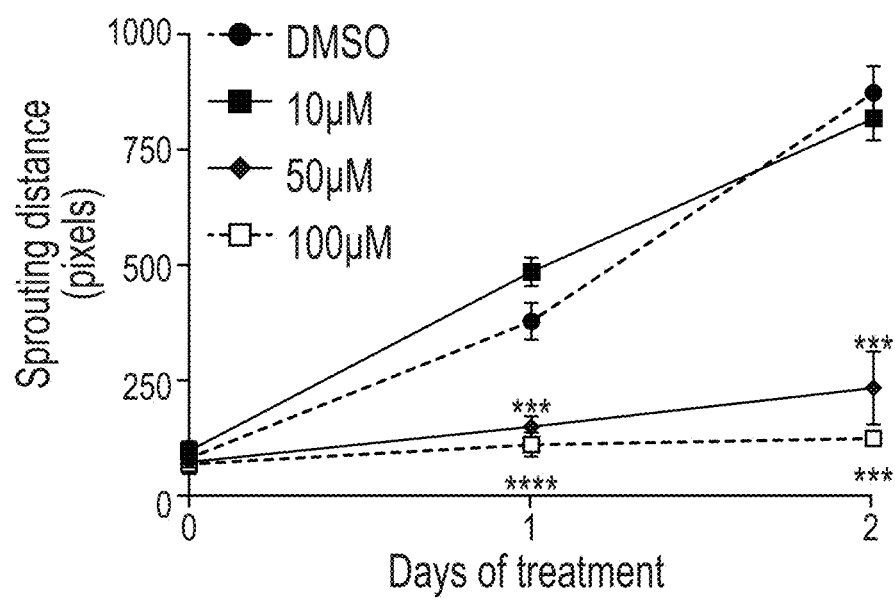

The FDA-approved antifungal drug, griseofulvin, has been in clinical use for over half a century. The primary antifungal mechanism of this compound is as a microtubule inhibitor. However, an off-target effect of this drug is inhibition of FECH. Griseofulvin alkylates the heme prosthetic group of cytochrome P450 in vivo, forming NMPP, the active site FECH inhibitor. Taking advantage of this phenomenon, HRECs were treated with griseofulvin and dose-dependent antiproliferative effects, inhibition of migration, and inhibition of tube formation similar to that observed with FECH knockdown were observed (FIGS. 9A-9C). The concentrations of griseofulvin needed to have effects were higher than those seen with NMPP (FIGS. 4E & 4F and 5A), likely due to incomplete alkylation of heme in griseofulvin-treated cells. However, this concentration (~10 μM or ~3.5 ng/mL) is 2.75 logs less than that attained in plasma during antifungal treatment of humans (1-2 μg/mL), suggesting that efficacy in vitro can be achieved in a clinically attainable concentration range. Further, griseofulvin inhibited formation of microvascular sprouts in the choroidal sprouting assay, an ex vivo model of ocular angiogenesis (FIG. 9D).

Figure 10A:
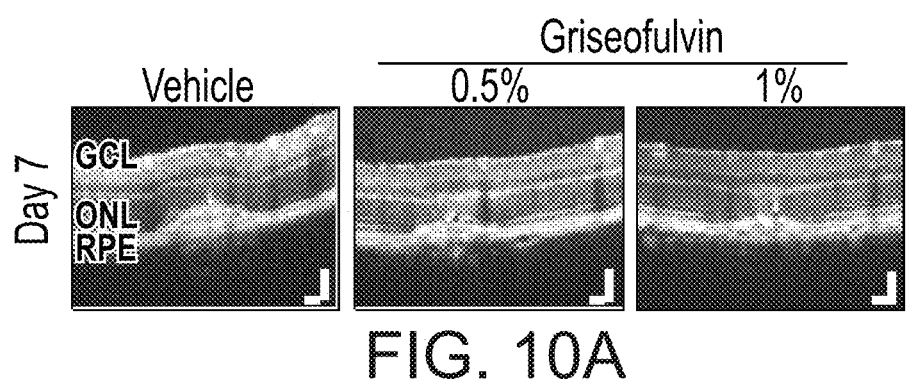
FIGS. 10A-10F depict inhibition by the antifungal drug griseofulvin of ocular neovascularization in vivo. Particularly, mice were fed ad libitum with 0.5% and 1% griseofulvin for one week prior to, and throughout CNV development and choroidal neovascularization was monitored by OCT (FIG. 10A) and confocal imaging of CNV lesions (FIG. 10B). The lesion volumes were measured from confocal images (FIG. 10C). The effect of single intravitreal injection of griseofulvin at time of laser treatment on choroidal neovascularization in L-CNV model is shown as monitored by OCT (FIG. 10D) and confocal imaging of CNV lesions (FIG. 10E). The CNV lesion volumes were measured using confocal images (FIG. 10F). The graphs show mean±SEM with n=6 mice per group. *, p<0.05; ****, p<0.0001. Scale bars for OCT images and immunostained choroids are 100 μm and 50 μm respectively.
Figure 10B:
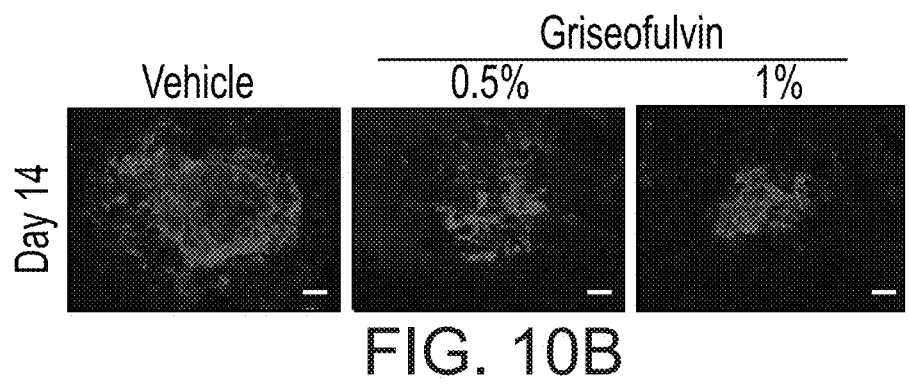
Figure 10C:
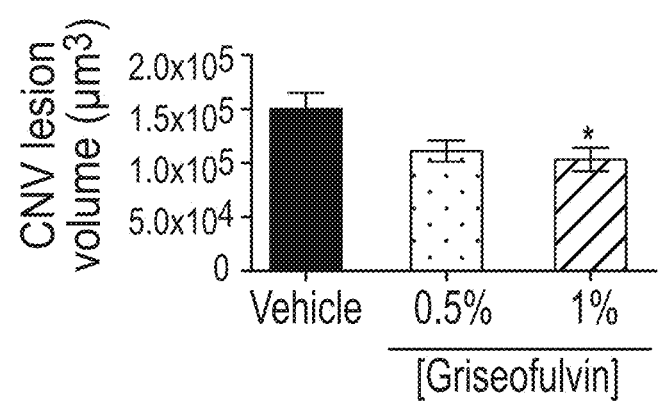
Figure 10D:
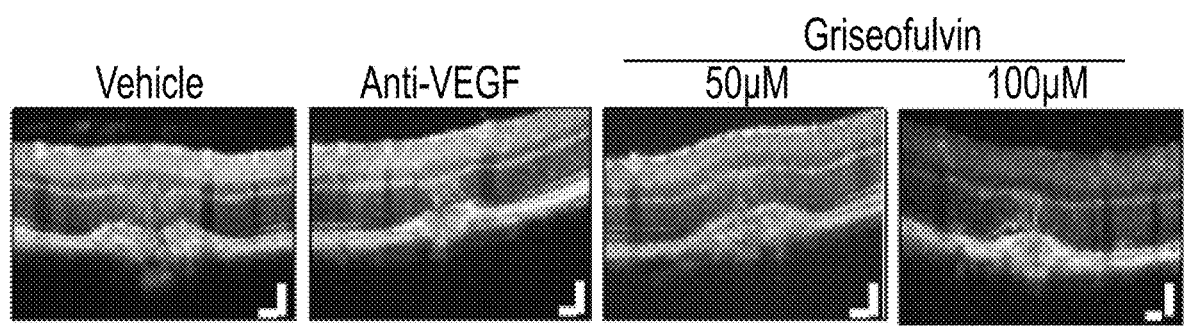
Figure 10E:
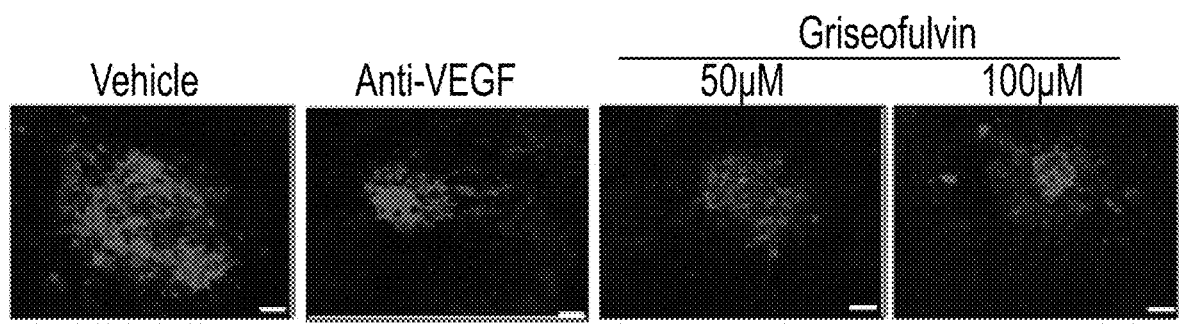
Figure 10F:
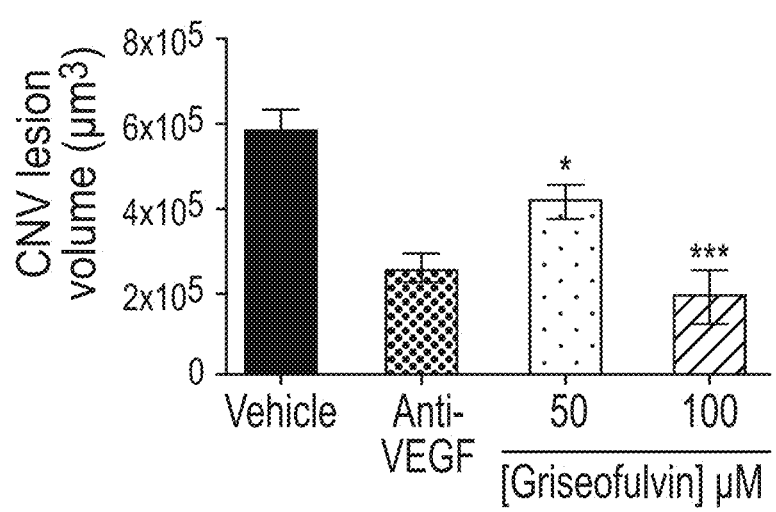

Griseofulvin was further tested as a therapy for L-CNV. Feeding of griseofulvin to L-CNV mice decreased neovascularization (FIGS. 10A-C). Similar, dose-dependent results were seen with intravitreal injection of the drug, the standard delivery for existing anti-VEGF agents (FIGS. 10D-10F).

The above Examples show a central role of ferrochelatase in ocular angiogenesis. The data provide the rationale for clinical testing of griseofulvin in neovascular eye disease, as well as developing novel, FECH-targeted therapies for treating the debilitating ocular and systemic diseases caused by neovascularization.

Particularly, using a photoaffinity based chromatographic technique FECH was identified as a protein binding partner of the antiangiogenic natural product, cremastranone. An accumulation of PPIX, the substrate for FECH, was observed in HRECs after treatment with cremastranone, suggesting that ferrochelatase activity is inhibited by cremastranone. Although, like other natural products, cremastranone likely exhibits polypharmacology, it exerts its antiangiogenic activity at least partially through inhibition of FECH activity, causing buildup of PPIX in HRECs.

FECH is indeed a mediator of angiogenesis. Lack of FECH activity caused inhibition of angiogenesis both in vitro and in vivo. More importantly, only HREC proliferation was inhibited in vitro while other ocular cell types tested did not show significant decreases in cell proliferation after FECH knock down. Even macrovascular HUVECs were not as profoundly affected by FECH depletion as the microvascular HRECs. These data reveal that retinal microvascular endothelial cells are particularly susceptible to FECH inhibition and are particularly sensitive to its depletion. The lack of cytotoxic effects of FECH inhibition leads to consideration of FECH as a therapeutic target for ocular neovascular disease, possibly with minimal side effects. Supporting this assertion, in the genetic disease erythropoietic protoporphyria (EPP), FECH activity is markedly reduced, but EPP patients infrequently present severe symptoms apart from skin photosensitivity.

It was further shown that the FDA-approved antifungal drug and FECH inhibitor, griseofulvin, inhibited ocular angiogenesis in the L-CNV mouse model when administered orally. Griseofulvin has been used widely for over half a century to treat fungal infections and is taken orally, often for months or years. An off-target side effect of this therapy is that griseofulvin causes the formation of NMPP, along with other alkylated porphyrins, primarily in liver. NMPP in turn acts as an active-site inhibitor of FECH. As with genetic ablation of FECH, apart from skin photosensitivity, no other major, common side effects are reported with systemic griseofulvin treatment of humans.

The fact that griseofulvin-fed mice showed decreased ocular neovascularization as compared to control mice is important as currently there are no oral drugs available for the treatment of ocular neovascularization. Further, although anti-VEGF biologics have been shown to halt or even reverse the progression of the disease, their systemic side effects are well known, they are expensive, and also significant patient populations (~30%) are not responsive or become refractory to the therapy. Since griseofulvin was also effective when delivered intravitreally, combination therapies of this drug with anti-VEGF biologics are an appealing possibility to increase efficacy and decrease side effects of existing treatments. Moreover, griseofulvin offers the promise of low-cost treatment as well as possible oral delivery, and thus might improve the standard of living of wet AMD patients if shown efficacious in clinical trials.

This written description uses examples to disclose the invention and also to enable any person skilled in the art to practice the present disclosure, including making and using any compositions and performing any incorporated methods. The patentable scope of the present disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method consisting of
   (a) steps for inhibiting ocular angiogenesis in an individual in need thereof, wherein the steps consist of administering an agent to the individual in order to inhibit ferrochelatase in the individual, the agent being selected from the group consisting of N-methylprotoporphyrin (NMPP); griseofulvin; antisense RNA; an agent for RNA silencing or an agent for RNA interference (RNAi) targeting ferrochelatase (FECH) RNA; an agent for CRISPR/Cas9-mediated genetic ablation of ferrochelatase (FECH) DNA; an agent for Zinc-finger nuclease-mediated genetic ablation of ferrochelatase (FECH) DNA; and combinations thereof, and optionally, administering one or more additional agents selected from the group consisting of ranibizumab; bevacizumab; aflibercept; pegpleranib; squalamine ((1S,2S,5S,7R,9R,10R, 11S,14R,15R)-N- {3-[(4-aminobutyl)amino]propyl }- 9-hydroxy-2,15-dimethyl-14-[(R2R,5R)-6-methyl-5-(sulfooxy)heptan-2- yl]tetracyclo[8.7.0.0/\{2,7 }.0 {11,15 }heptadecan-5-aminium); vorolanib; PAN-90806; TNP470; fumagillin (2E,4E,6E,8E)-10-{[R3R, 4S,5S,6R)-5-methoxy-4-[(2R)-2-methyl-3-(3-methyl-but-2- enyl)oxiran-2-yl]-1-oxaspiro[2,5]octan-6-yl] oxy}-10-oxodeca-2,4,6,8-tetraenoic acid); pigment epithelium derived factor (PEDF); endostatin; angiostatin; anecortave acetate; triamcinolone ((11β, 16α)-9-Fluoro-11,16,17,21-tetrahydroxypregna-1,4-diene-3,20-dione); and combinations thereof, wherein when the agent is griseofulvin, it is administered to achieve an intravitreal concentration of 10 μM to 500 μM of griseofulvin, and
   (b) simultaneously administering one or more pharmaceutically acceptable carriers.

2. The method of claim 1 wherein the agent is FECH siRNA, and the agent is administered to the individual in an amount of the siRNA to achieve an intravitreal concentration of 0.5 μM to 10 μM of the siRNA.

3. The method of claim 1 wherein the agent is in a pharmaceutical composition, and the composition comprises at least one pharmaceutically acceptable carrier.

4. The method of claim 3 wherein the composition is administered by oral administration, parenteral administration, injection, drop infusion preparations, or a suppository.

5. The method of claim 3 wherein the composition is administered as an eye drop or an eye ointment.

6. A method consisting of
(a) steps for treating ocular neovascular eye disease in an individual in need thereof, wherein the steps consist of administering an agent to the individual in order to inhibit ferrochelatase in the individual, the agent being selected from the group consisting of N- methylprotoporphyrin (NMPP); griseofulvin; antisense RNA; an agent for RNA silencing or an agent for RNA interference (RNAi) targeting ferrochelatase (FECH) RNA; an agent for CRISPR/Cas9-mediated genetic ablation of ferrochelatase (FECH) DNA; an agent for Zinc-finger nuclease-mediated genetic ablation of ferrochelatase (FECH) DNA; and combinations thereof, and optionally, administering one or more additional agents selected from the group consisting of ranibizumab; bevacizumab; aflibercept; pegpleranib; squalamine ((1S ,2S ,5S ,7R,9R,10R,11S,14R,15R)-N-{3-[(4-aminobutyl)amino]propyl}-9-hydroxy-2,15- dimethyl-14-{(2R,5R)-6-methyl-5-(sulfooxy)heptan-2- yl]tetracyclo[8.7.0.0^{2,7}.0^{11,15}]heptadecan-5-aminium); vorolanib; PAN-90806; TNP470; fumagillin (2E,4E,6E,8E)-10-{[R3R,4S,5S,6R)-5-methoxy-4-[(2R)-2-methyl-3-(3-methylbut-2- enyl)oxiran-2-yl]-1-oxaspiro[2,5]octan-6-yl]oxy}-10-oxo-deca-2,4,6,8-tetraenoic acid); pigment epithelium derived factor (PEDF); endostatin; angiostatin; anecortave acetate; triamcinolone ((11β,16)-9-Fluoro-11,16,17,21-tetrahydroxypregna-1,4-diene-3,20-dione); and combinations thereof, wherein when the agent is griseofulvin, it is administered to achieve an intravitreal concentration of 10 μM to 500 μM of griseofulvin, and
(b) simultaneously administering one or more pharmaceutically acceptable carriers.

7. The method of claim 5 wherein the agent is FECH siRNA, and the agent is administered to the individual in an amount of the siRNA to achieve an intravitreal concentration of 0.5 μM to 10 of the siRNA.

8. The method of claim 5 wherein the agent is in a pharmaceutical composition, and the composition comprises at least one pharmaceutically acceptable carrier.

9. The method of claim 8 wherein the composition is administered by oral administration, parenteral administration, injection, drop infusion preparations, or a suppository.

10. The method of claim 8 wherein the composition is administered as an eye drop or an eye ointment.

11. The method of claim 5, wherein the neovascular eye disease is selected from the group consisting of retinopathy of prematurity (ROP), "wet" age related macular degeneration (AMD), proliferative diabetic retinopathy (DR), pathological myopia, hypertensive retinopathy, occlusive vasculitis, polypoidal choroidal vasculopathy, uveitic macular edema, central retinal vein occlusion, branch retinal vein occlusion, corneal neovascularization, retinal neovascularization, ocular histoplasmosis, and neovascular glaucoma.

* * * * *